(12) United States Patent
Spenciner et al.

(10) Patent No.: US 11,728,033 B2
(45) Date of Patent: Aug. 15, 2023

(54) DYNAMIC ADAPTATION OF CLINICAL PROCEDURES AND DEVICE ASSESSMENT GENERATION BASED ON DETERMINED EMOTIONAL STATE

(71) Applicant: Medos International Sarl, Le Locle (CH)

(72) Inventors: David B. Spenciner, North Attleboro, MA (US); Alec Ginggen, Cincinnati, OH (US)

(73) Assignee: Medos International Sarl, Le Locle (CH)

( * ) Notice: Subject to any disclaimer, the term of this patent is extended or adjusted under 35 U.S.C. 154(b) by 127 days.

(21) Appl. No.: 16/877,889

(22) Filed: May 19, 2020

(65) Prior Publication Data

US 2020/0381117 A1 Dec. 3, 2020

Related U.S. Application Data

(60) Provisional application No. 62/854,179, filed on May 29, 2019.

(51) Int. Cl.
*G16H 50/20* (2018.01)
*G16H 70/20* (2018.01)
(Continued)

(52) U.S. Cl.
CPC ............. *G16H 50/20* (2018.01); *A61B 5/165* (2013.01); *G06Q 10/06316* (2013.01);
(Continued)

(58) Field of Classification Search
CPC ........ G16H 50/20; G16H 40/67; G16H 40/20; G16H 50/30; G16H 70/20; A61B 5/165; G06Q 10/06316
See application file for complete search history.

(56) References Cited

U.S. PATENT DOCUMENTS 11,387,000 B2 * 7/2022 Saliman .................. G16H 10/60
2018/0065248 A1 * 3/2018 Barral ..................... G06N 20/00
(Continued)

FOREIGN PATENT DOCUMENTS

EP            1868485 A2 * 12/2007  ............. A61B 17/02
TW         20140075 A  * 11/2012
WO    WO-2016138348 A1 *  9/2016  ............. A61B 34/20

*Primary Examiner* — Sheetal R Paulson

(57) ABSTRACT

Systems and methods are provided for determining an emotional state of a medical professional and dynamically generating clinical procedures that are adapted to the medical professional's emotional state, as well as an assessment of a medical device based on the determined emotional state. Observation data corresponding to a medical professional associated with a clinical procedure can be received and processed to determine an emotional state of the medical professional. The emotional state can be predicted using a first predictive model trained in a machine learning process. The determined emotional state can be provided to a second predictive model to provide one or more adapted clinical procedures. Device assessment data can also be used with the determined emotional state to determine an assessment of a medical device. The one or more adapted clinical procedures and the assessment of the medical device can be provided as an output.

19 Claims, 6 Drawing Sheets

(51) Int. Cl.
*G16H 50/30* (2018.01)
*G16H 40/67* (2018.01)
*G16H 40/20* (2018.01)
*A61B 5/16* (2006.01)
*G06Q 10/0631* (2023.01)

(52) U.S. Cl.
CPC ............. *G16H 40/20* (2018.01); *G16H 40/67* (2018.01); *G16H 50/30* (2018.01); *G16H 70/20* (2018.01)

(56) References Cited

U.S. PATENT DOCUMENTS

2019/0031097 A1* 1/2019 O'Herlihy ............. B60W 40/09
2021/0076966 A1* 3/2021 Grantcharov .......... A61B 5/352

* cited by examiner

DYNAMIC ADAPTATION OF CLINICAL PROCEDURES AND DEVICE ASSESSMENT GENERATION BASED ON DETERMINED EMOTIONAL STATE

RELATED APPLICATION

This application claims priority under 35 U.S.C. § 119(e) to U.S. Provisional Application No. 62/854,179, filed May 29, 2019, the entire contents of which are hereby expressly incorporated by reference herein.

BACKGROUND

Clinical procedures performed in a medical or healthcare setting can vary depending on a diagnosis and/or condition of a patient, the availability of appropriately trained medical professionals, the scope of insurance coverage held by the patient, as well as access to specific medical equipment to be used during a particular clinical procedure. The safe performance and successful outcome of clinical procedures can often be attributed to the training and skillset of the medical professionals performing the procedures, but can also be affected by the emotional state of the medical professionals. A medical professional who is not emotionally prepared to perform a challenging clinical procedure may make mistakes which could cause adverse consequences during or after the procedure, or could cause a life-threatening condition for the patient. For example, a surgeon performing a complicated vascular reconstruction procedure in an operating room may inadvertently avoid specific workflows associated with the procedure, in whole or in part, if the surgeon is experiencing a depressed or anxious emotional state. Similarly, a physician grieving over the loss of a relative may exhibit ambivalence or neglect when performing clinical procedures. The emotional state of medical professionals is an important consideration to ensure clinical procedures can be performed safely and as intended with regard to a particular patient's condition and/or diagnosis.

Machine learning is an application of artificial intelligence that automates the development of an analytical model by using algorithms that iteratively learn patterns from data without explicit indication of the data patterns. Machine learning is commonly used in pattern recognition, computer vision, language processing and optical character recognition and enables the construction of algorithms that can accurately learn from data to predict model outputs thereby making data-driven predictions or decisions. Machine learning can be utilized to develop a predictive model capable of determining an emotional state of a medical professional and dynamically adapting clinical procedures performed by the medical professional based on observation data. The adapted clinical procedures can be performed to ensure the procedure is performed in a safe manner and with a greater likelihood of performing the procedure successfully.

SUMMARY

In one aspect, methods for generating adapted clinical procedures based on a determined emotional state of a medical professional are provided. In one embodiment, the method can include receiving observation data corresponding to a medical professional associated with a clinical procedure. The method can also include determining an emotional state of the medical professional using the received observation data and a first predictive model trained to receive observation data and, in response to the receiving, provide an emotional state associated with the medical professional, the emotional state predicted in relation to one or more features included in the observation data. The method can further include determining one or more adapted clinical procedures using the determined emotional state and a second predictive model trained to receive the determined emotional state, and in response to the receiving, provide one or more adapted clinical procedures predicted in relation to the determined emotional state. The method can also include providing the one or more adapted clinical procedures. At least one or the receiving, the determining, and the providing can be performed by at least one data processor forming part of at least one computing system.

In another aspect, methods for providing an assessment of a medical device based on a determined emotional state are provided. In one embodiment, the method can include receiving observation data corresponding to a medical professional associated with a clinical procedure. The method can further include receiving device assessment data of corresponding to a medical device associated with the medical procedure. The method can also include determining an assessment of the medical device. The assessment can be determined based on the determined emotional state and the received device assessment data. The method can further include providing the assessment of the medical device. At least one or the receiving, the determining, and the providing can be performed by at least one data processor forming part of at least one computing system.

Non-transitory computer program products (i.e., physically embodied computer program products) are also described that store instructions, which when executed by one or more data processors of one or more computing systems, causes at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including a connection over a network (e.g. the Internet, a wireless wide area network, a local area network, a wide area network, a wired network, or the like), via a direct connection between one or more of the multiple computing systems, etc.

DESCRIPTION OF DRAWINGS

These and other features will be more readily understood from the following detailed description taken in conjunction with the accompanying drawings, in which.

Figure 1:
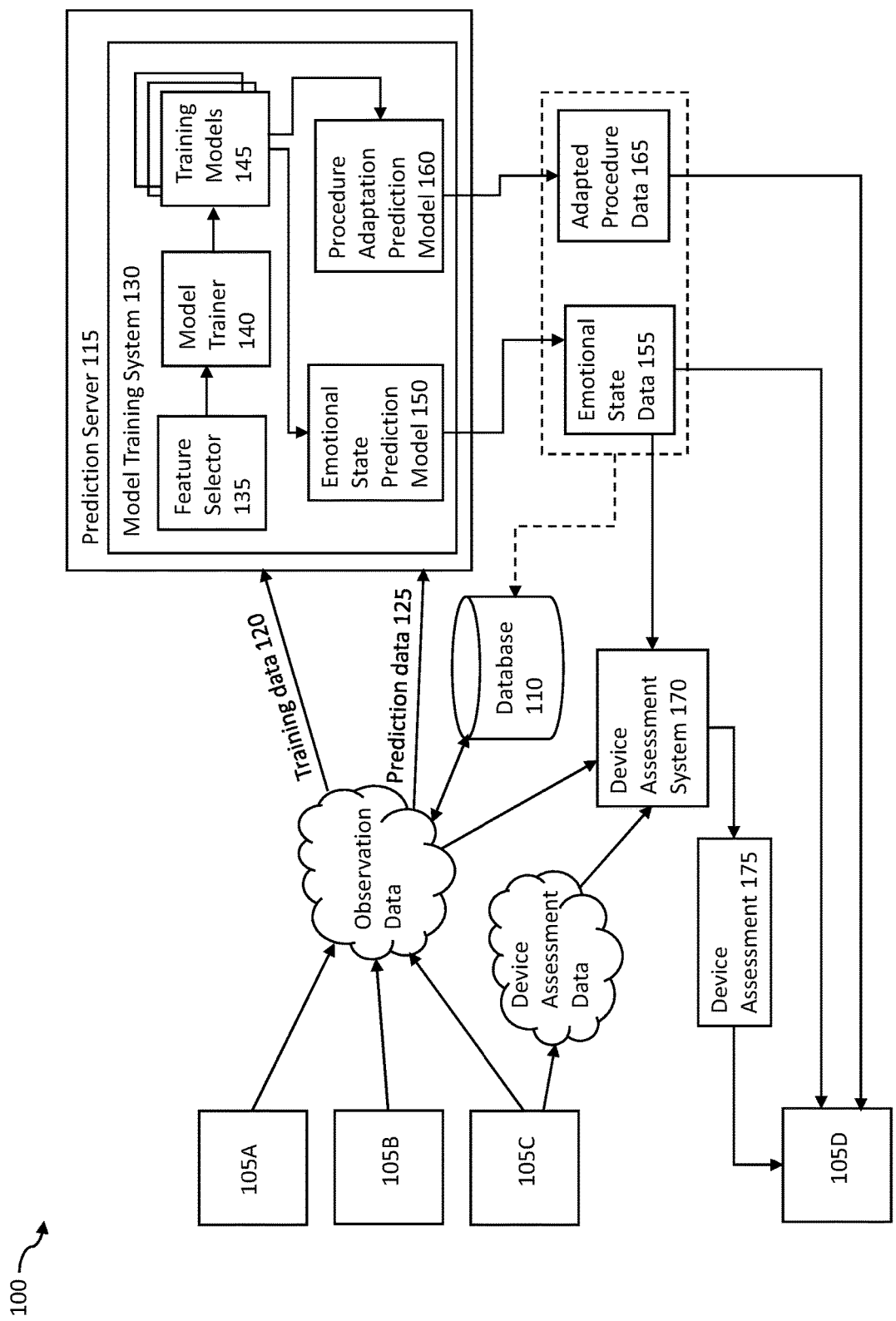
FIG. 1 is a block diagram illustrating an example architecture for determining an emotional state of a medical professional and dynamically generating adapted clinical procedures using observation data and a predictive model.

It is noted that the drawings are not necessarily to scale. The drawings are intended to depict only typical aspects of the subject matter disclosed herein, and therefore should not be considered as limiting the scope of the disclosure.

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Medical professionals can experience emotional states that can have adverse effects on their ability to perform particular clinical procedures. The ability to successfully and safely perform complicated medical procedures can be hindered if a surgeon, for example, is feeling tired, overwhelmed, depressed, or confused. The surgeon may not be able to fully focus on and perform various tasks that may be involved in a particular medical procedure, such as an arthroscopy or heart valve replacement surgery, as a result of a negative emotional state which can lead to mistakes which may be unsafe and may put the patient at risk.

The modern clinical environment includes technology which can be leveraged to determine an emotional state of a medical professional. Imaging and sensor systems can be configured within an operating room or similar environment in which clinical procedures are performed and can be used to collect observation data which may be indicative of an emotional state of a medical professional. A variety of sensor data can also be collected from sensors that can be configured within equipment, instruments, as well as sensors which may be worn by a medical professional such as sensors that are affixed directly to the body of the medical professional and sensors that may be configured within clothing or personal protective equipment worn by the medical professional.

Existing procedure monitoring systems may utilize image data to evaluate and review clinical procedures but lack the sophistication to determine an emotional state of a medical professional participating in the procedure and to further dynamically provide modifications in a clinical procedure while the procedure is occurring. The modifications may alter how a particular sequence of tasks associated with a clinical procedure is to be performed and can further include providing additional support in the form of training materials, alternate equipment or instruments, alternate personnel resources, as well as modifications in the environment in which the clinical procedure is being performed. By determining the emotional state of a medical professional and generating adapted or modified clinical procedures, the risk of errors leading to an unsuccessful procedure can be reduced while the overall safety of the patient and likelihood of a successful procedure outcome can be increased.

Embodiments of systems and corresponding methods for determining an emotional state of a medical professional and dynamically generating adapted clinical procedures using observation data and a predictive model are discussed herein. However, embodiments of the disclosure can be employed for determining an emotional state and generating alternate, enhanced, adapted, or modified workflows based on observation data associated with non-medical personnel and procedures without limit.

FIG. 1 is a block diagram illustrating an example architecture 100 for determining an emotional state of a medical professional and dynamically generating adapted clinical procedures using observation data and a predictive model. The example architecture 100 can also be configured to determine an assessment of a medical device using a determined emotional state and/or device assessment data. The architecture 100 includes clients 105, database 110, and prediction server 115, which can be communicatively coupled over a network.

As shown in FIG. 1, the architecture 100 includes clients 105, e.g., clients 105A-105D. The clients 105, such as clients 105A-105C, can be configured to acquire and/or store observation data, such as data that can be sensed or otherwise observed from medical professionals participating in a particular clinical procedure. For example, the observation data can be transmitted from operating room camera systems, body-mounted sensors, sensors that can be integrated within instruments, sensors that can be configured within protective clothing or equipment, or computing devices used to collect survey data from a medical professional. In some embodiments, the client 105 can include a camera or imaging system configured within an operating room to monitor movements by medical professionals during a clinical procedure. In some embodiments, the client 105 can include one or more computing devices configured to store observation data that may be collected from a medical professional in a survey provided to the medical professional to determine his/her emotional state in advance of participating in a clinical procedure. In some embodiments, the client 105 can transmit facial recognition, thermal imaging, and/or eye motion data as the observation data. The observation data can be transmitted from the clients 105 as streaming data, such as streaming video data that is collected and transmitted in real-time or near real-time. In some embodiments, the clients 105 can receive, store, and transmit device assessment data associated with a particular medical device.

The clients 105 can include a large-format computing device or any other fully functional computing device, such as a desktop computer or laptop computer, can transmit observation data to prediction server 115. Additionally, or alternatively, other computing devices, such as small-format computing devices can also transmit observation data to the prediction server 115. Small-format computing devices can include a tablet, smartphone, personal digital assistant (PDA), or any other computing device that can have more limited functionality compared to large-format computing devices. For example, client 105A can include a laptop configured with a web-browser displaying a series of questions or a survey that can be provided to the medical professional to determine his/her emotional state prior to participating in a clinical procedure. Client 105B can include a camera or imaging system configured to obtain observation data and to transmit observation data associated with the movements or motions of a particular medical professional during a particular clinical procedure in which the medical professional is participating. Client 105C can include historical observation data stored in memory of the client 105C, such as facial recognition data, hand and limb motion data, and/or eye movement data associated with a particular medical professional that can be used to provide observation data from past clinical procedures as training data in a machine learning process. Client 105C can also include device assessment data associated with a medical device, a surgical field, a medical procedure, and/or a medical professional. The device assessment data can include data such as surgical-field specific data, surgeon-specific data, and patient-specific data. Additionally, client 105D can include a computing device configured to display predetermined workflows associated with a clinical procedure, determined emotional states of medical professionals participating in a current clinical procedure, safety and compliance metrics associated with the clinical procedure, as well as modified workflow sequences, alternate equipment, and/or training materials that may be provided based on the observation data received from clients 105A-105C.

The architecture 100 also includes a database 110 that can store observation data received from the clients 105 or from other computing devices or cameras via a network. In some embodiments, the database 110 can store historical observation data associated with past clinical procedures for which a particular medical professional was present. The database 110 can also store observation data that can be used as training data, such as training data 120, which can be used to train one or more predictive models. In some embodiments, the database 110 can also store observation data that can be used as prediction data, such as prediction data 125, which can be used by the prediction server 115 to determine an emotional state of a medical professional and dynamically generate or provide modifications or changes in a particular clinical procedure, for example as emotional state data 155 and/or the adapted procedure data 165. As shown via the dashed lines, the database 110 can further store the emotional state data 155 and/or the adapted procedure data 165 provided by the prediction server 115.

As further shown in FIG. 1, observation data can be transmitted from the clients 105 and/or from the database 110 to the prediction server 115. In some embodiments, the observation data includes training data 120 that is transmitted to the prediction server 115 for use in a machine learning process. In some embodiments, the training data 120 can also include observation data associated with a specific medical professional, or a specific clinical procedure. In some embodiments, the emotional state data 155 and the adapted procedure data 165 may be provided by one or more prediction models, such as trained prediction models 150 and/or 160. In some embodiments, the emotional state data 155 and the adapted procedure data 165 may be provided or generated manually via users interacting with a GUI configured to receive inputs for use in the machine learning process configured on the prediction server 115. The training data 120 is used to train a machine learning algorithm in a machine learning process in order to determine an emotional state of a medical professional and dynamically provide or generate adapted clinical procedures, such as emotional state data 155 and the adapted procedure data 165 based on a variety of received observation data. In some embodiments, the observation data includes prediction data 125 that is transmitted to a prediction server 115 as inputs to the generated model that was trained in the machine learning process using the training data 120. In some embodiments, the observation data, provided as prediction data 125, can also be provided to the prediction server 115 as inputs to one or more predictive models developed using supervised or unsupervised machine learning methods. The observation data can include emotional state data, facial recognition data, thermal imaging data, eye motion data, emotional survey response data, sensor data associated with an instrument used by the medical professional during a particular clinical procedure, as well as sensor data collected from one or more sensors configured on the medical professional's body or within an article of clothing or protective equipment worn by the medical professional. In some embodiments, the observation data can be provided to the device assessment system 170 in order to determine a device assessment.

As shown in FIG. 1, the architecture 100 includes a prediction server 115 configured to receive the observation data and provide adapted or modified clinical procedure data, such as the emotional state data 155 and the adapted procedure data 165. The prediction server 115 includes a model training system 130 configured to train a predictive model in a supervised or unsupervised machine learning process for use in determining an emotional state of a medical professional and dynamically generating adapted clinical procedures that are output as the emotional state data 155 and the adapted procedure data 165. In broad overview, the prediction server 115 functions in the training aspect of a machine learning process to receive observation data from a client 105, such as a camera, a sensor, a computing device, and/or observation data stored in database 110 as training inputs and generates one or more training models for use in determining an emotional state of a medical professional and/or dynamically generating enhanced, modified, alternate, or substitute aspects of the clinical procedure as the emotional state data 155 and the adapted procedure data 165.

The model training system 130 configured on the prediction server 115 includes a feature selector 135, which is used in the supervised training aspect of the machine learning process to select features of data in the observation data. The model training system 130 also includes a model trainer 140 which uses a selected machine learning algorithm or network to process the selected features of data and generates a new training model 145. The new training model 145 can be subsequently used outside of the machine learning process as a first prediction model, such as emotional state prediction model 150 configured to predict emotional state 155 for particular features of observation data received as prediction data 125. Additionally, or alternatively, the new training model 145, or a variant thereof, can also be used outside of the machine learning process as a second prediction model, such as the procedure adaptation prediction model 160 configured to predict adapted procedure data 165 for particular features of observation data received as prediction data 125.

As shown in FIG. 1, the prediction server 115 includes a feature selector 135. During the training aspect of the supervised machine learning process, the feature selector 135 receives observation data and selects subsets of features in the observation data which are used as training input to train the selected machine learning algorithm. For each selected subset of features in the training input 120, the selected machine learning algorithm can be trained to determine an emotional state of the medical professional associated with the observation data and to determine adaptations to clinical procedures, such as the emotional state data 155 and the adapted procedure data 165 that may be associated with the subset of features for which the selected machine learning algorithm was trained. The trained machine learning algorithm can then be output as a newly trained prediction model (e.g., trained models 150 and 160), which can then be subsequently applied to observation data (e.g., prediction data 125) to determine the emotional state data 155 and/or the adapted procedure data 165. The emotional state data 155 can include determinations of a medical professional's emotional state, such as whether the medical professional is happy, sad, depressed, excited, frustrated, or anxious. The adapted procedure data 165 can include modifications to the procedure workflow, equipment usage, operating room environment, and participating personnel, as well as the provision of training materials that may be associated with the clinical procedure being performed or the equipment and operating room environment being used to perform the procedure by the medical professional.

The prediction server 115 also includes a model trainer 140. In some embodiments, the model trainer 140 can be included in the prediction server 115. In other embodiments, the model trainer 140 can be located remotely from the prediction server 115. During the training aspect of the supervised machine learning process, the model trainer 140 receives the training input including the selected subsets of features of the observation data from the feature selector 135 and iteratively applies the subsets of features to the previously selected machine learning algorithm to assess the performance of the algorithm. In a supervised machine learning process, the algorithm processes the training input, the model trainer 140 learns patterns in the training input that map the machine learning algorithm variables to the target output data (e.g., the emotional state data 155 and the adapted procedure data 165) and generates one or more training models 145 that capture these relationships. For example, as shown in FIG. 1, the model trainer 140 outputs the training models 145. As further shown in FIG. 1, one training model 145 that is output can be subsequently deployed as a first standalone trained prediction model, such as the trained emotional state prediction model 150. A second training model 145 can be output and subsequently deployed as a second standalone trained prediction mode, such as the trained procedure adaptation prediction model 160.

As further shown in FIG. 1, the prediction server 115 includes a trained first prediction model 150, such as the emotional state prediction model 150. The emotional state prediction model 150 can include an algorithm that has been generated as a result of the model training performed during the training aspect of a supervised or unsupervised machine learning process. Once trained, the emotional state prediction model 150 can operate outside of a machine learning process to receive observation data as prediction data 125 and to determine an emotional state of a medical professional. The determined emotional state data 155 can be further used as inputs (either as training data 120 or as prediction data 125) to the procedure adaptation prediction model 160 in order to further generate and/or provide adapted procedure data 165 based on the for observation data associated with a medical professional and a particular clinical procedure for which the medical professional is participating. For example, the emotional state prediction model 150 provides a determined emotional state as emotional state data 155 based on processing the observation data. The emotional state data 155 can include states of emotion that the medical professional may be experiencing, such as fear, anger, sadness, joy, disgust, trust, anticipation, surprise, love, remorse, sorrow, depression, excitement, anxiety, ambivalence, boredom, interest, violence, distraction, fatigue, surprise, or apprehension In some embodiments, the emotional state prediction model 150 can be deployed on the prediction server 115 or can be deployed in a configuration that is remotely located from, yet communicatively coupled to, the prediction server 115. For example, the first prediction model 150 can be located in a remote, cloud computing environment or a virtualized computing environment that is coupled to the clients 105 via a network.

As further shown in FIG. 1, the model training system 130 includes a trained second prediction model 160. The second prediction model, such as the procedure adaptation prediction model 160 can include one or more predictive algorithms trained in a supervised or unsupervised machine learning process to receive observation data and determined emotional state data 155 as inputs, for example, as prediction data 125, and to determine changes, modifications, substitutions, additions, enhancements, and/or adaptations of a particular clinical procedure. For example, based on receiving the observation data and the determined emotional state data 155, the procedure adaptation prediction model 160 can generate or provide an abbreviated procedure workflow or generate or provide an indication that an alternate piece of equipment may be used in the procedure. In some embodiments, the procedure adaptation prediction model 160 can be configured within or separately from the model training system 130. In some embodiments, the procedure adaptation prediction model 160 can be configured within the prediction server 115. In some embodiments, the procedure adaptation prediction model 160 can be communicatively coupled to the prediction server 115 but located remotely from the prediction server 115. For example, the procedure adaptation prediction model 160 can be located in a remote, cloud computing environment or virtualized computing environment that is coupled to the clients 105 via a network.

As shown in FIG. 1, the architecture 100 also includes a device assessment system 170. In some embodiments, the device assessment system 170 can be configured within a client 105. In some embodiments, the device assessment system 170 can be configured within a server, such as the prediction server 115. The device assessment system 170 can include computer-readable instructions which when executed can cause the system to receive emotional state data 155 generated from the prediction server 115, device assessment data generated, stored in and/or transmitted from a client 105, as well as observation data. The received emotional state data 155, device assessment data, and or observation data can be provided as inputs to an algorithm or computational model configured to receive the emotional state data 155, the device assessment data, and/or the observation data as inputs and to determine a device assessment 175. The device assessment 175 can be transmitted to a client 105, such as client 105D, to be provided to a user via a display, stored in memory of the client 105D. In some embodiments, the device assessment data and the device assessment 175 provided by the device assessment system 170 can be stored in the database 110. Further details regarding the operation of the device assessment system 170 will be provided in relation to FIG. 5.

Figure 2A:
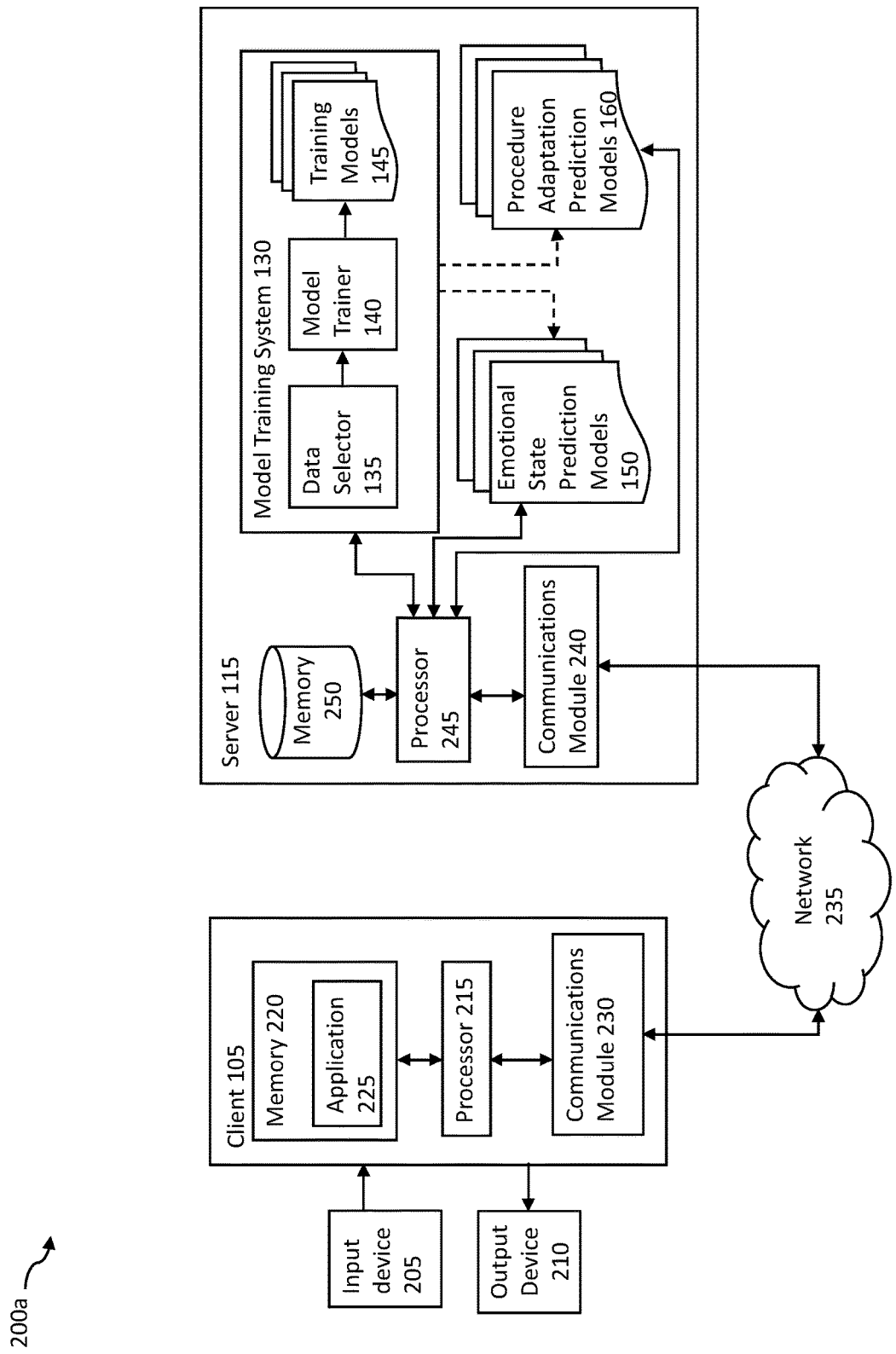
FIGS. 2A-2B illustrate example block diagrams of systems for determining an emotional state of a medical professional and dynamically generating adapted clinical procedures using observation data and a predictive model.

FIG. 2A is an example block diagram of a system 200a for determining an emotional state of a medical professional and dynamically generating adapted clinical procedures based on observation data using machine learning according to some embodiments. System 200a includes an input device 205 and an output device 210 coupled to a client 105, such as any of the clients 105 described in relation to FIG. 1.

As shown in FIG. 2A, the client 105 includes a processor 215 and a memory 220 storing an application 225. The client 105 also includes a communications module 230 connected to network 235. System 200a also includes a server 115, such as the prediction server 115 described in relation to FIG. 1. The server 115 includes a communications module 240, a processor 245 and a memory 250. The server 115 also includes a model training system 130. The model training system 130 includes a feature selector 135, a model trainer 140 and one or more training models 145. The model training system 130 includes similar components and performs similar operations as the prediction server 115 shown in FIG. 1, except where indicated otherwise in the foregoing description. The server 115 also includes one or more trained emotional state prediction models 150 trained via a supervised or unsupervised machine learning process and one or more trained procedure adaptation prediction models 160 which have also been trained via a supervised or unsupervised machine learning process. The emotional state prediction models 150 and the procedure adaption prediction models 160 are shown to be output using dotted lines to indicate that the training models 145, which were output during the training performed in one of the machine learning processes can be one or more trained prediction models, such as the one or more emotional state prediction models 150 and the procedure adaptation prediction models 160.

As shown in FIG. 2A, the system 200a includes an input device 205. The input device 205 receives user input and provides the user input to client 105. The input device 205 can include a keyboard, mouse, microphone, stylus, game controller, joy stick, hand/or any other device or mechanism used to input observation data to an application or user interface on a client, such as client 105. In some embodiments, the input device 205 can include haptic, tactile or voice recognition interfaces to receive the user input, such as on a small-format device. In some embodiments, the input device 205 can be a camera configured to acquire observation data during a clinical procedure performed by the medical professional. The camera can be configured to capture color or black and white images or video, thermal imaging data, infrared imaging data, or the like. In some embodiments, the input device 205 can include a sensor or network of sensors that can be deployed in relation to the environment in which a particular medical procedure is occurring and for which a particular medical professional is participating. The sensors can include sensors which can be deployed in the operating room environment as well as sensors worn on the body or configured within the clothing worn by a medical professional participating in a particular medical procedure. For example, the sensors can include sensors configured to monitor temperature, breathing rate, heart rate, facial patterns, pupil dilation, perspiration and moisture vapor transmission rates, galvanic skin response, and the like. In some embodiments, the input device 205 can a sensor or camera configured within a piece of personal protective equipment worn by the medical professional, such as a facemask. In some embodiments, the inputs device 205 can be a camera or sensor that can be embedded or configured within an instrument used during a procedure, such as a monitor or a retractor.

The system 200a also includes a client 105. The client 105 communicates via the network 235 with the server 115. The client 105 receives input from the input device 205. The client 105 can be, for example, a large-format computing device, such as large-format computing device 105 as described in relation to FIG. 1, a small-format computing device (e.g., a smartphone or tablet), such as small-format computing device 105, or any other similar device having appropriate processor, memory, and communications capabilities to transmit observation data. The client 105 can be configured to receive, transmit, and store observation data associated with determining an emotional state of a medical professional and dynamically generating adapted clinical procedure data based on the observation data received from client 105. The client 105 can be configured with one or more software applications. The software applications can include web-based applications as well as applications that can be directly hosted or configured on the client 105. For example, the software applications can be configured to provide surveys to a medical professional in advance of participating in a particular medical procedure. The surveys can include a series of questions that can be customized to aid in determining an emotional state of the medical professional. In some embodiments, the clients 105 can include software applications configured to display or provide indications of a procedure workflow, including the sequence of steps that must be performed during the procedure. The clients 105 can also include computing devices configured within the operating room environment to display equipment options, training materials, and/or alternate personnel who can be of assistance in or otherwise perform a particular procedure. In some embodiments, the client 105 can be interfaced with an input device 205, such as a camera or heart rate monitor that can be configured with appropriate wired or wireless communication interfaces necessary to transmit observation data to the server 115 for use in determining an emotional state of the medical professional and generating adapted procedure data.

As further shown in FIG. 2A, the client 105 includes a processor 215 and a memory 220. The processor 215 operates to execute computer-readable instructions and/or data stored in memory 220 and transmit the computer-readable instructions and/or data via the communications module 230. The memory 220 can store computer-readable instructions and/or data associated with determining an emotional state of a medical professional and dynamically generating adapted procedure data based on the received observation data. For example, the memory 220 can include a database of observation data received by the client 105, such as a database 110 as shown in FIG. 1. The memory 220 includes an application 225. The application 225 can be, for example, a sensor monitoring application configured to receive observation data from one or more sensors, such as one or more cameras, configured within an operating room, or within a clinical laboratory setting to observe a medical professional and coupled to the client 105 for use in determining an emotional state of the medical professional and generating adapted procedure data.

As shown in FIG. 2A, the client 105 includes a communications module 230. The communications module 230 transmits the computer-readable instructions and/or the observation data stored on or received by the client 105 via network 235. The network 235 connects the client 105 to the server 115. The network 235 can include, for example, any one or more of a personal area network (PAN), a local area network (LAN), a campus area network (CAN), a metropolitan area network (MAN), a wide area network (WAN), a broadband network (BBN), the Internet, and the like. Further, the network 235 can include, but is not limited to, any one or more of the following network topologies, including a bus network, a star network, a ring network, a mesh network, a star-bus network, tree or hierarchical network, and the like.

As further shown in FIG. 2A, the server 115 operates to receive, store and process the computer-readable instructions and/or the observation data generated and received by client 105. In some embodiments, the server 115 can receive observation data directly from one or more clients 105. The server 115 can be any device having an appropriate processor, memory, and communications capability for hosting a machine learning process. In certain aspects, one or more of the servers 115 can be located on-premises with client 105, or the server 115 can be located remotely from client 105, for example in a cloud computing facility or remote data center of a hospital or other facility associated with performing the clinical procedures. The server 115 includes a communications module 240 to receive the computer-readable instructions and/or the observation data transmitted via network 235. The server 115 also includes one or more processors 245 configured to execute instructions that when executed cause the processors to train a predictive model or network during the training phase of a machine learning process and to determine an emotional state of a medical processional so that adapted or modified clinical procedures can be further provided based on the observation data and a determined emotional state received during the prediction phase of a machine learning process. In some embodiments, the processor 245 can be a graphical processing unit (GPU). The improved procedure adaptation and device assessment system described herein can leverage the processing power of GPUs to reduce model training time and increase prediction execution time.

The server 115 also includes a memory 250 configured to store the computer-readable instructions and/or observation data associated with determining an emotional state of a medical professional and dynamically generating adapted clinical procedures based on the received observation data. In some embodiments, the memory 250 can store data which may be used in the training phase of the machine learning process. For example the memory 250 can store time-series datasets of observation data, such as datasets including sequences of images capturing the body language, gestures, or motions of the medical professional being observed over time or in regard to past clinical procedures the medical professional has performed. Additionally, or alternatively, the memory 250 can store observation data that is received in real-time or near real-time, as well as previously provided observation data. In some embodiments, memory 250 can store one or more training models, such as the training models 145 used during the training of a machine learning process to generate a trained prediction models, such as the emotional state prediction models 150 and the procedure adaptation prediction models 160 configured to provide emotional state data 155 and adapted procedure data 165, respectively, that corresponds to the observation data provided to application 225. In some embodiments, memory 250 can store one or more trained models, such as the emotional state prediction model 150 and the procedure adaptation prediction model 160 that were similarly generated during a machine learning process and were trained to determine an emotional state of a medical professional and to further determine and provide modified or altered clinical procedures for different types of sensors, cameras, clinical procedures, medical professionals, patients, or the like observation data. In some embodiments, the memory 250 can store one or more machine learning algorithms or networks that will be used to generate the one or more training models 145. In some embodiments, the memory 250 can store observation data that may be received from client 105 over a period of time and can be used as a training dataset in the machine learning process in order to train a prediction model. In some embodiments, the memory 250 can store one or more trained prediction models that are variants of the emotional state prediction models 150 and/or the procedure adaptation prediction models 160. The variant trained prediction models were generated with respect to alternate sets of features in the observation data as compared to features commonly associated with a particular emotional state and/or a particular set of clinical procedures.

As shown in FIG. 2A, the server 115 includes a model training system 130. The model training system 130 functions in a machine learning process to receive observation data as training inputs, e.g. training data 120, and processes the inputs to train one or more training models. In some embodiments, the training data 120 can also include a variety of sensor data providing observations of a medical professional that were affirmatively associated with a particular emotional state. The training data 120 can also include common procedural adaptations that have led to successful procedural outcomes when it was previously determined a medical professional was experiencing a particular emotional state. The model training system 130 includes a feature selector 135, a model trainer 140, and one or more training models 145. In some embodiments, the training models 145 that are generated and output as a result of the machine learning processes are configured on server 115 as standalone components on server 115. For example, the trained emotional state prediction models 150 and the procedure adaptation prediction models 160 that are configured on server 115 to process the observation data to determine an emotional state of a medical professional and further dynamically provide one or more adapted clinical procedures based on the observation data.

The model training system 130 is configured to implement a supervised or unsupervised machine learning process that receives observation data and/or a determined emotional state of the medical professional as training inputs and generates a training model that can be subsequently used to determine an emotional state of a medical professional and to dynamically provide adaptions to clinical procedures or workflows based on the emotional state of the medical professional and the observation data that may be received by one or more of the clients 105. The components of the machine learning process operate to receive observation data as training input, select unique subsets of data within the observation data, use a machine learning algorithm to train a model based on the subset of data in the training input and generate a training model that can be output as a trained prediction model used for future predictions based on a variety of received observation data.

As shown in FIG. 2A, the model training system 130 includes a feature selector 135. The feature selector 135 operates in the supervised or unsupervised machine learning process to receive the observation data and to select a subset of features from the inputs which will be provided as training inputs to a machine learning algorithm. In some embodiments, the feature selector 135 can select a subset of features corresponding to different categories of cameras, sensors, or other configurations of input devices that were used to provide and provide the observation data such that the machine learning algorithm or network will be trained to determine an emotional state for the medical professional and can further provide adapted clinical procedures based on the selected subset of features in the observation data and/or the determined emotional state. In some embodiments, the feature selector 135 can select a subset of features corresponding to the type of observation data provided as inputs to the clients 105, such as data that may be related to individual medical professionals, specific clinical procedures, and/or different configurations of operating rooms or equipment associated used during particular clinical procedures.

During the supervised machine learning process, the feature selector 135 provides the selected subset of features to the model trainer 140 as inputs to a machine learning algorithm to generate one or more training models. A wide variety of machine learning algorithms can be selected for use including algorithms such as long short-term memory (LSTM), Recurrent Neural net architectures (RNN), Convolutional Auto Encoders, support vector regression, ordinary least squares regression (OLSR), linear regression, logistic regression, stepwise regression, multivariate adaptive regression splines (MARS), locally estimated scatterplot smoothing (LOESS), ordinal regression, Poisson regression, fast forest quantile regression, Bayesian linear regression, neural network regression, decision forest regression, boosted decision tree regression, artificial neural networks (ANN), Bayesian statistics, case-based reasoning, Gaussian process regression, inductive logic programming, learning automata, learning vector quantization, informal fuzzy networks, conditional random fields, genetic algorithms (GA), Information Theory, support vector machine (SVM), Averaged One-Dependence Estimators (AODE), Group method of data handling (GMDH), instance-based learning, lazy learning, and Maximum Information Spanning Trees (MIST).

The generated training models, e.g., trained emotional state prediction models 150 and the trained procedure adaptation prediction models 160, are then capable of receiving observation data from outside of the machine learning process in which they were trained and determine an emotional state of a medical professional and to provide modified clinical procedures which have been adapted based on the medical professionals determined emotional state.

As shown in FIG. 2A, the trained emotional state prediction models 150 that were generated as a result of performing the supervised machine learning process, can receive observation data and process the inputs to output an emotional state associated with a medical professional for whom the observation data was collected. For example, the trained emotional state prediction models 150, that were produced in the supervised or unsupervised machine learning process, can be subsequently be included in an artificial intelligence system or an application configured to receive observation data, for example facial recognition data, as prediction inputs and to process the data in order to output an emotional state of the medical professional. In some embodiments, the processor 245 can store the determined emotional state that was output from the trained emotional state prediction models 150 in memory 250. In other embodiments, the outputted emotional state data can be forwarded to communications module 240 for transmission to the client 105 via network 235. Once received by the client 105, the outputted emotional state data 155 associated with the medical professional performing a particular clinical procedure can be transmitted to output device 210, such as a display, printer, portable hard drive or other storage device. In some embodiments, the determined emotional state data 155 can be provided to the server 115 as prediction data 125 as inputs to the procedure adaptation prediction models 160 in order to determine and provide one or more procedural adaptations that can be provided to the medical professional during the procedure to increase the likelihood of achieving a successful procedure outcome or to perform the procedure in a more safe manner.

As shown in FIG. 2A, the server 115 can also include one or more trained procedure adaptation prediction models 160. The procedure adaptation prediction models 160 can be trained in a supervised or unsupervised machine learning process configured on the server 115. During the machine learning process, the procedure adaptation prediction models 160 can be trained to receive observation data, including the previously determined emotional state, as inputs to a predictive model trained to provide adapted procedure including modified procedural workflows, alternate equipment, additional or alternate personnel, training materials for a procedure or piece of equipment used in the procedure, and changes to an operating room environment such as lighting or temperature. The procedure adaptation prediction models 160 can be implemented using an similar or alternative machine learning algorithms as the emotional state prediction models 150, such as such as long short-term memory (LSTM), Recurrent Neural net architectures (RNN), Convolutional Auto Encoders, support vector regression, ordinary least squares regression (OLSR), linear regression, logistic regression, stepwise regression, multivariate adaptive regression splines (MARS), locally estimated scatterplot smoothing (LOESS), ordinal regression, Poisson regression, fast forest quantile regression, Bayesian linear regression, neural network regression, decision forest regression, boosted decision tree regression, artificial neural networks (ANN), Bayesian statistics, case-based reasoning, Gaussian process regression, inductive logic programming, learning automata, learning vector quantization, informal fuzzy networks, conditional random fields, genetic algorithms (GA), Information Theory, support vector machine (SVM), Averaged One-Dependence Estimators (AODE), Group method of data handling (GMDH), instance-based learning, lazy learning, and Maximum Information Spanning Trees (MIST).

Figure 2B:
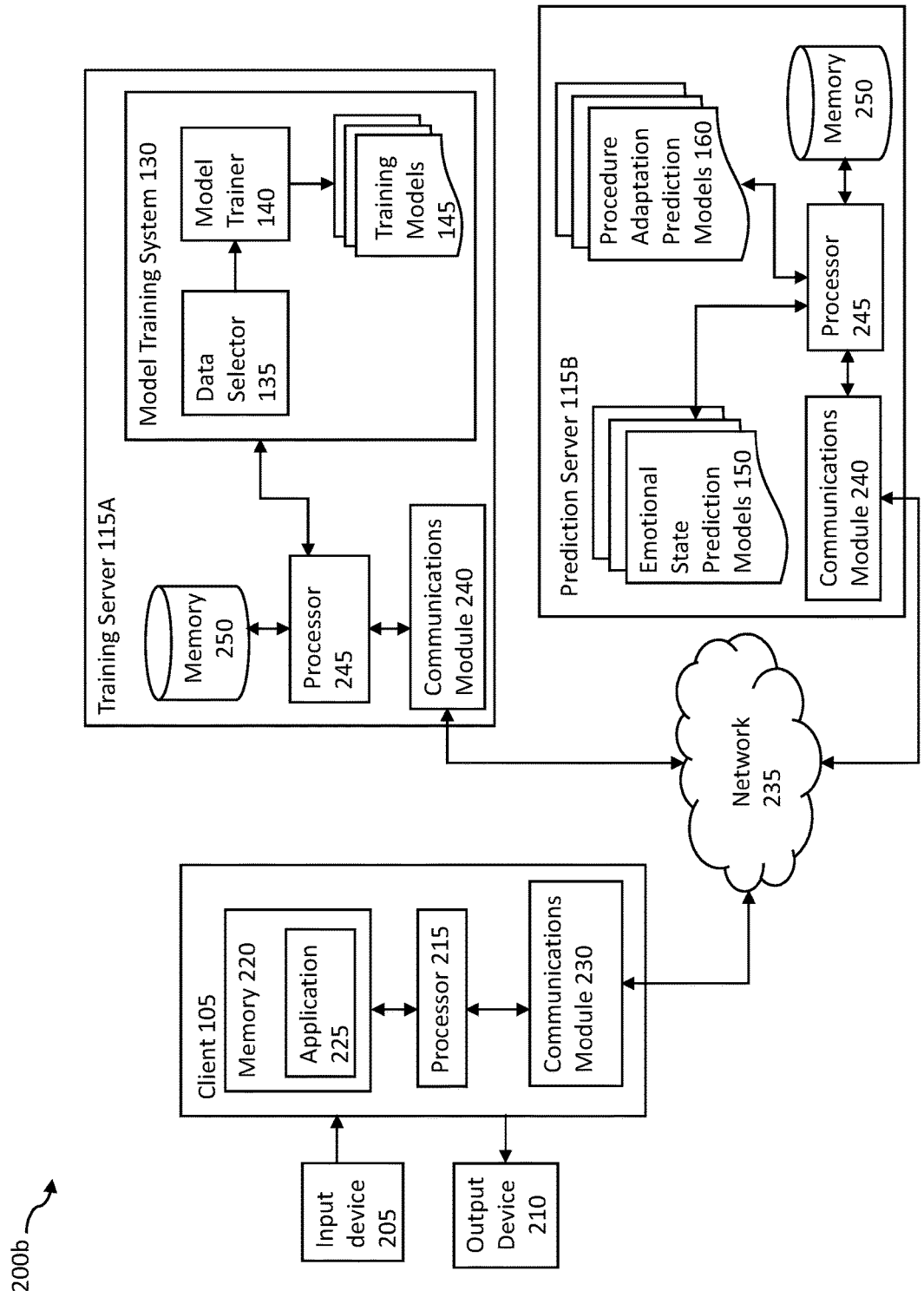

FIG. 2B illustrates an example block diagram of a system 200*b* using a machine learning process configured on a model training server 115A. The individual components and functionality of each component shown and described in relation to model training server 115A in FIG. 2B are identical to the components and respective functionality shown and described in relation to server 115 of FIG. 2A with the exception that the model training server 115A shown in FIG. 2B does not include one or more trained emotional state prediction models 150 or one or more trained procedure adaptation prediction models 160 as shown in FIG. 2A.

Instead, as shown in FIG. 2B, the system 200b includes a training server 115A that is configured separately from the trained prediction models, e.g., the emotional state prediction models 150, that are now configured on the prediction server 115B. The prediction server 115B includes components and functionality similar to the server 115 shown in FIG. 2A with the exception that the prediction server 115B shown in FIG. 2B does not include a model training system, such as the model training system 130 shown in FIG. 2A. The prediction server 115B shown in FIG. 2B includes one or more trained prediction models. The trained prediction models configured on the prediction server 115B include the emotional state prediction models 150 and the procedure adaptation prediction models 160, which can be implanted as algorithms that were generated from a machine learning process, and have been trained in the machine learning process to determine an emotional state of a medical professional based on observation data provided to or stored on a client 105 and to provide adaptations to clinical procedures based on the determined emotional state of the medical professional and/or the observation data. For example, upon receiving observation data from a client, for example client 105, the emotional state prediction models 150 can be employed to provide one or more predicted emotional states associated with a medical professional based on the received observation data. Similarly, the procedure adaptation prediction models 160 can also be configured on the prediction server 115B. The procedure adaptation prediction models 160 can be employed to provide one or more changes, modifications, or adaptations to a particular clinical procedure based on the received observation data and the emotional state determined using the emotional state prediction models 150.

As shown in FIG. 2B, system 200b also includes a training server 115A. The training server 115A includes a model training system 130 which implements a supervised or unsupervised machine learning process and includes a feature selector 135, a model trainer 140, and one or more training models 145. In some embodiments, the training server 115A can be located in the same location as prediction server 115B. In other embodiments, the training server 115A can be located in a remote location, for example in a second data center that is separately located from the hospital data center or clinical procedure facility location where the prediction server 115B is located. In some embodiments, the training system 130, configured on the training server 115A, can be utilized to evaluate different machine learning algorithms or networks and can generate one or more alternate training models 145. For example, based on using different subsets of features in the received observation data as the training inputs to a different machine learning algorithm and process, the model training system 130 can train and output a different training model 145 than the trained emotional state prediction models 150 and/or the trained procedure adaptation prediction models 160 configured on prediction server 115B which can have been trained using a separate machine learning algorithm and process.

The training system 130 can also be configured with a machine learning process to train and output one or more trained prediction models that are capable of determining an emotional state of a medical professional and generating adapted clinical procedures based on live, delayed, or historical observation data which may have been collected in regard to the medical professional in the past and can be stored in memory 220 or memory 250. In some embodiments, the training system 130 can generate a model, such as trained emotional state prediction models 150 and/or trained procedure adaptation prediction models 160 which can be capable of determining an emotional state of a medical professional and generating adapted clinical procedures when one or more features of the observation data which are traditionally used to determine a particular aspect of the medical professional's emotional state or for a particular clinical procedure are not available in the observation data. As such, the emotional state and resulting clinical procedure modifications provided based on partial or incomplete observation data can be optimized based on the additional observation data which may identify features which can be used to provide the determined emotional state and/or the modified clinical procedures. For example incomplete emotional state survey data or facial recognition data in which a portion of the medical professional's face is obscured by a mask or other form of personal protective equipment can be supplemented with heart rate data, breathing data, and/or sensor data associated with a sensor worn by the medical professional.

The training system 130 can also be configured with a supervised or unsupervised machine learning process to train and output multiple models, such as the emotional state prediction models 150 and the procedure adaptation prediction models 160 that have been trained in the machine learning process based on non-overlapping or partially overlapping sets of training data. In some embodiments, the different sets of training data that are associated with multiple models can be implemented on the prediction server 115B to create a more robust system that includes an ensemble or collection of models or networks. In such embodiments, the prediction server 115B can provide determined emotional states and adapted clinical procedures based on observation data acquired during different types of procedures, using different equipment, or being performed in different operating room environments. Additionally, or alternatively, the prediction server 115B can provide determined emotional states and adapted clinical procedures based on observation data associated with different observation data formats, observation data file types, different sensor types or other statistically correlated patterns observed in the received observation data. In this way, the model or ensemble of models can be trained to provide determined emotional state and adapted clinical procedure data as outputs in situations when certain observation data which are used in a given prediction model may be missing or incomplete.

Figure 3:
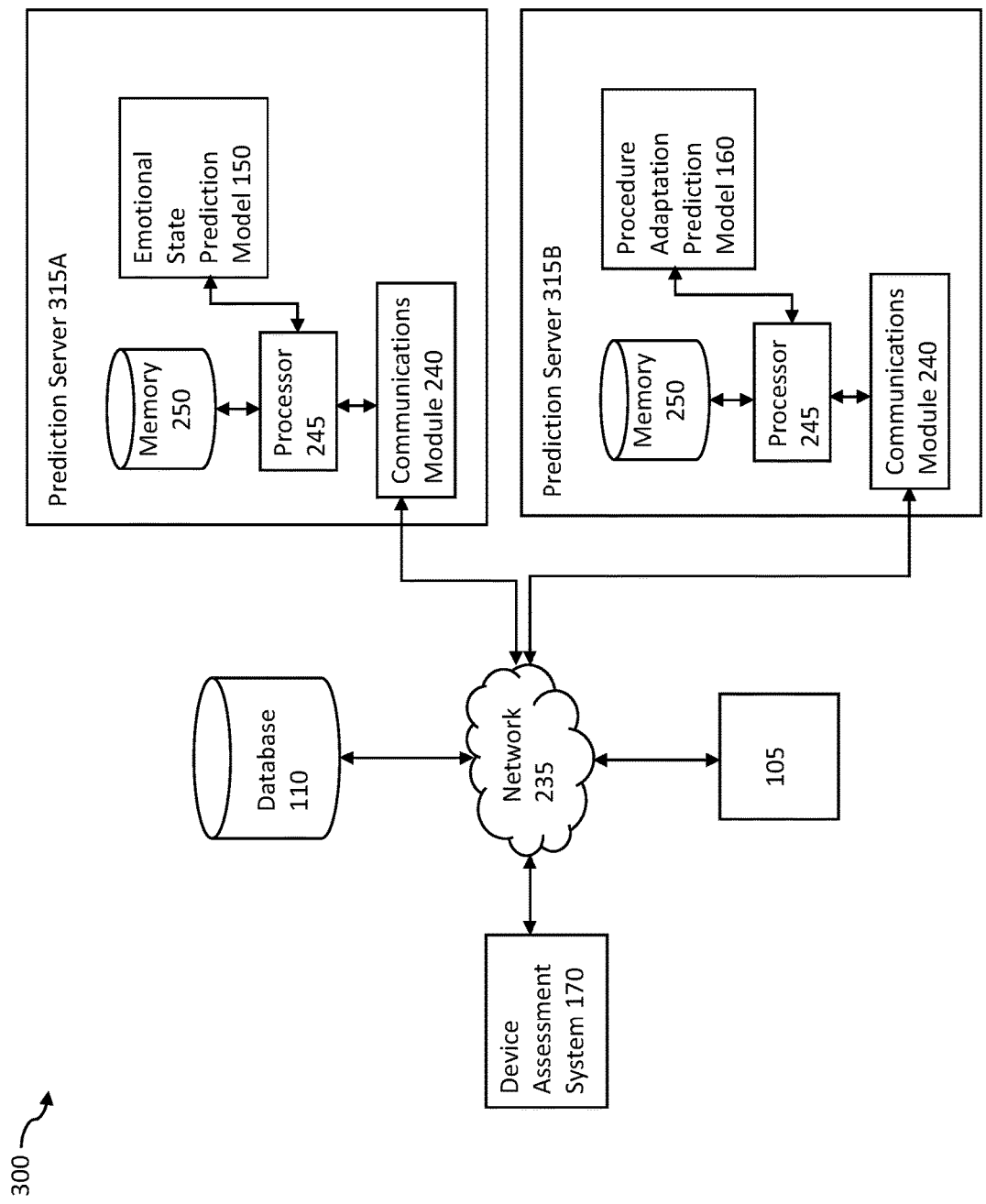
FIG. 3a is a block diagram illustrating one exemplary embodiment of an architecture for training a model to determining an emotional state of a medical professional and dynamically generating adapted clinical procedures based on observation data received as inputs.

FIG. 3 is a block diagram illustrating the example client and server from the architecture 100 of FIG. 1 in an exemplary deployed procedure adaptation and device assessment system 300. The block diagram of the deployed procedure adaptation and device assessment system 300 includes an example client 105 similar to the client described in relation to architecture 100 of FIG. 1. The deployed procedure adaptation and device assessment system 300 also includes a prediction server 315A configured with one or more trained emotional state prediction models 150 and a second prediction server 315B, deployed remotely or separately from the prediction server 315A. For example, prediction server 315A can be configured in a cloud or virtualized computing environment associated with the primary data center at which the clinical procedure may be occurring. Prediction server 315B can be configured in a computing environment located at a different location, such a remote data center with expanded computing resources. The prediction server 315B can be configured with a second prediction model, such as one or more procedure adaptation prediction models 160. The prediction servers 315A and 315B are similar to the prediction server 115B described in relation to the system 200*b* of FIG. 2B, according to certain aspects of the disclosure.

As shown in FIG. 3, the client 105, the database 110, and the servers 315A and 315B are connected over the network 235. The client 105 and each of the servers 315A and 315B can be configured to exchange data that can be used to determine emotional states of medical professionals and adapted clinical procedures associated with a medical professional being observed by an input device of the client 105 or by the client device 105 itself. Emotional states provided by prediction server 315A can include determinations that a medical professional is experiencing an emotional state of anger, fear, sadness, joy, or the like. The provided emotional state can be then used to determine one or more adaptations to a particular clinical procedure. Adaptation can include additions, modifications, substitutions, or removal of steps or tasks to be performed for a particular clinical procedure, personnel substitution, equipment substitution, training provision, changes to the clinical environmental where the procedure is occurring, or the like. In some embodiments, the determined emotional state data can also be used to provide or generate alerts or notifications based on determining anomalous, negative, or potentially harmful emotional states which may be associated with the received observation data. Additionally, the client 105 and the servers 315A and 315B may share observation data stored in database 110 that can be used in the deployed procedure adaptation and device assessment system 300 in order to provide determined emotional states and clinical procedure adaptations based on stored observation data. The observation data stored in the database 110 can include observation data associated with one or more medical professionals, historical observation data, as well as observation data that is associated with different configurations of cameras, sensors, clinical procedure environments, particular clinical procedures, or the like.

The servers 315A and 315B each include a communications module 240, a processor 245, and a memory 250 that includes one or more machine readable storage mediums containing program instructions for causing a computer to determine emotional states of a medical processional and to provide adapted clinical procedures based on observation data and/or the determined emotional state. The processors 245 of the servers 315A and 315B are configured to execute instructions, such as instructions physically coded into the processors 245, instructions received from software in memory 250, or a combination of both. For example, the processor 245 of the server 315A can execute instructions to determine the emotional state and to provide adapted clinical procedures based on observation data and/or a determined emotional state that may be output to a client 105. Similarly, the processor 245 of the server 315B can execute instructions to provide determined emotional states and clinical procedure data based on observation data and/or a determined emotional state which can be further output to a client 105.

As further shown in FIG. 3, the procedure adaptation and device assessment system 300 can also include a device assessment system 170. The device assessment system 170 can include computer readable instructions configured to implement an algorithm or computational model capable of generating device assessments 175 based on received data including device assessment data, operational data, and/or determined emotional state data 155.

The techniques described herein may further be implemented as method(s) that are performed by physical computing device(s); as one or more non-transitory computer-readable storage media storing instructions which, when executed by computing device(s), cause performance of the method(s); or, as physical computing device(s) that are specially configured with a combination of hardware and software that causes performance of the method(s).

Figure 4:
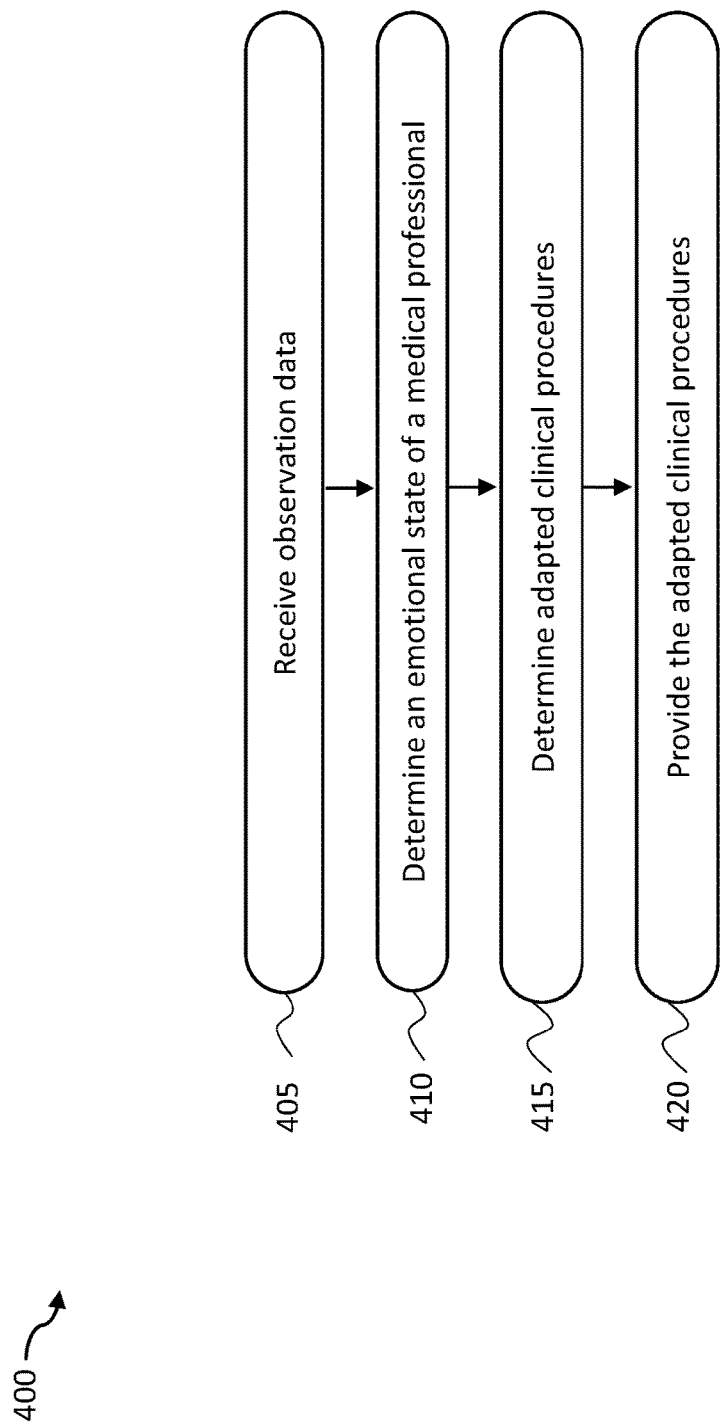
FIG. 4 is a flowchart illustrating one exemplary embodiment of a method for determining an emotional state of a medical professional and dynamically generating adapted clinical procedures using observation data and a predictive model using the client/server architecture of FIG. 1.

FIG. 4 is a flow diagram illustrating an exemplary embodiment of a method 400 for determining an emotional state of a medical professional and generating adapted clinical procedures based on observation data using the client/server architecture described in relation to FIGS. 1, 2A, and 2B and the trained emotional state prediction models 150 and/or the trained procedure adaptation prediction models 160 generated in a machine learning process using the training system 200*a* and 200*b*, as shown and described in relation to FIGS. 2A and 2B. In certain aspects, embodiments of the method 400 can include greater or fewer operations than illustrated in FIG. 4 and the operations can be performed in a different order than illustrated in FIG. 4.

For example, in operation 405, a client 105 receives an input including a plurality of observation data. The observation data may include a previously determined emotional state as well as observation data collected from a variety of client devices 105 that may be arranged in relation to the medical professional and/or the operating room or clinical environment in which the medical professional is performing or participating in a procedure. For example, an operating room can be configured with a camera system coupled to a computing device. The camera system may allow image data to be collected and transmitted to the prediction server 115 where it can be received as observation data. The image data may include observations of the medical professional in the clinical procedure setting and can include facial recognition data. The observations can include observations of the medical professional's body parts, such as their hands and/or eyes. In another example, a computing device 105 can be coupled to sensors on the medical professional's body and/or personal equipment that is worn by the medical professional. The sensor data can include a variety of physiological data that can be observed from the medical professional including, but not limited to, the medical professional's heart rate, breathing rate, perspiration rate, skin temperature, core temperature, facial motions or movements, hand gestures, arm gestures, or the like.

In some embodiments, a client 105 can receive the observation data from a database, such as database 110. The observation data may be historical observation data or may be live, streaming observation data that is received by the client in real-time or near real-time.

Upon receiving the observation data, the client 105 can transmit the observation data to a server, such as server 115. In some embodiments, the observation data can be transmitted to the server 115 as training data 120. In other embodiments, the observation data can be transmitted to the server 115 as prediction data 125. During the training phase of a machine learning process, the client 105 and/or the database 110 can transmit the input, as training data 120 to the model training server 115A of FIG. 2B. During the prediction phase of the machine learning process, the client 105 and/or the database 110 can provide prediction data 125 to the prediction server 115B of FIG. 2B. The inputs can be transmitted from the client 105 and/or the database 110 to the server 115 via the network 235.

In operation 410, the server 115 determines an emotional state of a medical professional. The server 115 determines the emotional state of the medical professional based on observation data via the emotional state prediction models 150. When the server 115 receives prediction data 125, the server 115 can apply the trained emotional state prediction model 150 generated as a result of the training phase of the machine learning process to the transmitted inputs and can provide a determined emotional state data for the medical professional based on the received observation data. For example, based on image observation data observing the medical professionals facial expressions, an emotional state can be determined. When the observation data includes such facial recognition data, features of the medical professionals face present in the image data can be associated with one or more emotional states and the predictive model can output a determined emotional state based on associations between the observed facial patterns and emotional states that are correlated to such facial patterns. For example, image data showing a clinician who is frowning or fails to make eye contact with others individuals can be associated with a sad, depressed, or frustrated emotional state. As described herein, a predictive model can be trained to process features of the observation data to provide a determined emotional state for the medical professional which can be output as emotional state data 155 and provided to a second predictive model for use in determining adaptations to clinical procedures based on the determined emotional state.

In operation 415, the server 115 determines adapted clinical procedures. Based on determining the emotional state of the medical professional in operation 410, the server 115 can receive the determined emotional state from the database 110 or as emotional state data 155 which can be provided as prediction data 125 to the procedure adaptation prediction model 160 in order to determine modifications, adaptations, or changes to a particular clinical or medical procedure in which the medical professional is participating. The emotional state data 155 as well as other observation data can be received by the server 115 and processed using a predictive model trained in a machine learning process to provide adaptations of the procedure. For example, based on receiving observation data observing the medical professional exhibiting slow, sluggish, or otherwise abnormal, or perhaps unsteady movements, the server 115 can provide adaptations of the procedure the medical professional is participating in. The adaptations can include providing equipment in a more proximal location, altering the lighting in the environment in which the procedure is being performed, changing the temperature of the environment in which the procedure is being performed, providing supporting personnel resources to further assist the medical professional perform the procedure. When the previously determined emotional state data 155 is also used as prediction data 155 in addition to the observation data, the procedure adaptation prediction model 160 can provide procedure adaptations related to the medical professional's emotional state. For example, continuing the previous example, where the medical professional was determined to have a sad, depressed, or frustrated emotional state, the procedure adaptation prediction model 160 can provide adaptations such as notifications to supporting or supervising staff about the medical professionals state, generating additional precautionary workflows or measures to ensure additional verifications or quality review checks are performed for procedure tasks, as well as causing the provision of reminders or training materials associated with the medical procedure being performed. A variety of adaptations are available which may be specific to the medical procedure being performed or may be specific to the medical professional themselves. For example, if a medical professional is known to have a favored or preferred piece of equipment or a preferred configuration of the operating room environment during a particular procedure, upon determining the emotional state of the medical professional as sad or frustrated, for example, the procedure adaptation prediction model 160 can be trained to determine the preferences of the medical professional should be provided. As such, the preferred item of equipment or configuration of the procedure environment can be output as a procedure adaptation.

A variety of clinical adaptions can be determined and provided by the procedure adaptation and device assessment system 300. A non-limiting set of procedural adaptations and device assessments are described herein. In some embodiments, the adapted clinical procedures can include causing a verification of an obligatory "time out" prior to the procedure starting. If the surgeon doesn't look up at a camera, the procedure would not be allowed to start. In some embodiments, the system 300 can determine and provide a recommendation to stop the case, especially if the medical professional's emotional state is determined to be angry or confused. In some embodiments, the system 300 can cause the volume of music in the procedure environment to be increased or decreased. In some embodiments, the system 300 can provide adapted clinical procedures including recommendations of different sized instruments or implants if the observation data indicates the medical professional is struggling to place or otherwise manipulate an article used in the procedure. In some embodiments, the system 300 can provide clinical adaptations including changing to a more or less conservative rehabilitation program for a patient. In some embodiments, the system 300 can provide clinical adaptations including asking the medical professional whether or not cases or procedures scheduled later in the day should be postponed. In some embodiments, the system 300 can provide clinical adaptations including opening a video chat with an on-duty mentor or supervising medical professional. In some embodiments, the system 300 can provide clinical adaptations including training materials which can be provided after the procedure has been completed to attending or support staff who are associated with the medical procedure. The training materials can include preferences of the medical professional which were observed during the medical procedure when the medical professional exhibited frustration or confusion and include recommendations for adaptations that can reduced or alleviate the frustrated or confused emotional state experienced by the medical professional during the procedure. Similarly, the procedure adaptations system 300 can provide feedback for medical device manufactures when a medical professional exhibits frustration with specific instruments or equipment. Hospital administrators could also use the provided feedback to select commoditized systems and thereby prioritize equipment or instruments which produced low levels of frustration or stress for medical professionals during particular procedures.

In operation 420, the server 115 provides the adapted clinical procedures. The server 115 determines and provides the adapted clinical procedures based on the observation data and/or the determined emotional state via the procedure adaptation prediction models 160. The server 115 can then provide the adapted clinical procedures. The server 115 can provide the adapted clinical procedures in a variety of direct or indirect manners to one or more clients 105 which are coupled to the server 115 and are associated with the clinical procedure in which the medical professional is participating. For example, the server 115 can cause one or more clients 105 to display training information, provide or generate an alarm or notification, and/or generate suggestions for alternate equipment, instruments, and/or personnel resources. In some embodiments, the server 115 can provide the adapted clinical procedures audibly, visually, or textually. For example, the adapted procedures can include a change in the sequence of tasks to be performed during a particular procedure, and the server 115 can provide the updated sequence of tasks on a display within the procedure environment. Similarly, the server 115 can provide the adapted procedures by displaying training materials about the procedure, information about a drug to be administered during the procedure, and/or availability of alternate equipment, drugs, procedural tasks, or personnel which are likely to ensure the safe completion of the procedure. In some embodiments, the server 115 can cause a change in the environment in which the procedure is occurring, such as changing the temperature, lighting, humidity levels, or the arrangement and positioning of equipment.

The provision of adapted clinical procedures can create a safer procedure environment, improved the emotional state of the medical professional, and provide procedural adaptations which are more likely to lead to a successful procedure outcome based on the medical professional's emotional state. In some embodiments, when the medical professional is determined to have a confident, happy, joyous or otherwise more positive emotional state, the system may provide fewer or different procedural adaptations as the medical professional may be more able to perform the procedure safely and successfully. In other embodiments, when the emotional state of the medical professional is determined to be depressed, sad, ambivalent, or otherwise more negative, the system may provide procedural adaptations that can have a more direct or immediate impact on ensuring the procedure is performed safely and successfully.

Clinical adaptions can be provided by the procedure adaptation and device assessment system 300 in a variety of manners. A non-limiting example of providing adaptations are described herein. In some embodiments, the adapted clinical procedures can include providing uniform resource locators (URLs) or links to executable content in a web-browser that can be directed to teaching web-sites, such as Vumedi. The links could be pre-loaded by a medical professional in advance of the procedure so that key aspects of the procedure are already available to the medical professional during the procedure. In such an example, the clinical adaptations can further include ghosted images of previous surgeries that can be overlaid atop live images from procedure being performed to remind the medical professional about specific aspects or tasks associated with the procedure. In some embodiments, the clinical adaptations can be provided as a list of alternate procedures considered to be "bail-outs." In some embodiments, the clinical adaptations can be provided as a list of seldom or commonly used instruments or equipment which other medical professionals performing a similar procedure have used. In some embodiments, the procedure adaptation and device assessment system 300 can detect and calculate mechanical advantages that might be gained if the medical professional was positioned differently relative to a patient, piece of equipment, or instrument. In such an example, the clinical adaptation can include a recommendation to adjust the configuration of the patient, equipment, or an instrument, such as increasing a stool height to gain mechanical advantage during a knee-replacement procedure.

The procedure adaptations system 300 described herein can also enable assessment of the percentage of procedural steps performed by an attending surgeon as compared to those performed by a fellow or a resident. Such assessment could be provided based on the observation data and identifying where the medical professional was looking and/or the placement of their hands or equipment being used. This could be useful in determining whether a medical professional, such as an attending surgeon, is a good teacher and allows fellows or residents to perform some of the procedure steps themselves. In this example, the procedure adaptation and device assessment system 300 could also enable tracking and determination of experience levels prior to determining whether a fellow or resident has completed an amount of training. Such data could be further used to determine personnel and/or resource allocations. For example, it could be determined that some procedures require additional staff while others can be safely performed using fewer or different staff. Continuing this example, the observation data could be used to determine billing and reimbursement decision as it allows assigning a percentage of the procedure tasks among multiple individuals.

The procedure adaptation and device assessment system 300 can be further utilized as a kind of "black-box" recording system to determine and record the emotional state of medical professionals and others in the clinical environment in which the procedure is occurring. In this way, distinctions can be made about whether an issue was caused by inattentiveness or manual error, due to errors or malfunctions of equipment, instruments, or implants, as well as issued arising from undetectable or inevitable causes, such as a physiological anomaly present within the patient. This observation data and the resulting analysis could be provided to hospital administrators, medical equipment and device manufacturers to aid in assessing the usability, efficiency and effectiveness of medical equipment and/or devices used during a particular procedure. This observation data and the resulting analysis can also be provided to hospital administrators, medical equipment and device manufacturers to improve training, procedural steps, and evaluation of "worst-case" scenario workflows during a particular procedure.

An exemplary use case employing the procedure adaptation and device assessment system 300 described herein can include assessing a medical device used during a procedure, such as a meniscal repair. A hospital administration may desire to gain feedback about the efficiency and utilization of a medical device used during the meniscal repair procedure in order to determine if the device represents a cost-effective tool and one that is liked and readily used by surgeons. Typically, a medical professional, such as a surgeon, will advocate for a particular device that they prefer. However, their preference can be biased as a result of ongoing relationships with medical device sales representatives or consultants. The hospital administration may take into account the medical professionals' preferences along with device costs, contractual obligations, and/or procurement requirements in order to determine a list of devices the hospital administration considers as acceptable for use during a particular procedure. One drawback to this determination is that very little data is collected to demonstrate which medical device is actually best for the medical professional and their patients.

Using the procedure adaptation and device assessment system 300 described herein, observation data can be combined and analyzed to create a more complete assessment of the usability and efficiency of various medical devices. The observation data may be initially collected to determine an emotional state of the medical professional. Additional inputs of device assessment data, such as observation data that is associated with assessing a medical device in relation to the surgical field, patient, and surgeon can be received and analyzed to determine an assessment of the device. A person skilled in the art will appreciate that the device assessment can be conducted in conjunction with or independent of the determination of the emotional state of the medical professional.

For example, during the meniscal repair procedure, a surgeon's face may be partially obscured while conducting the procedure in a sterile environment. The emotional state of the surgeon can be determined based on the received observation data which can include peak and time-based distributions of the surgeon's facial temperature, core temperature, and axillary temperature. In addition, the observation data can include changes in the surgeon's hand position relative to the medical device, as well as hand tremors that can be detected based on image data associated with the surgeons' hand movements. The observation data can also include data associated with the surgeon's pupil size, the presence or absence of perspiration, the extent and presence of changes in facial movements, such as when the surgeon may wrinkle or contract muscles in their forehead. Additionally, or alternatively, the observation data can include data indicating the presence or absence of pauses during the procedure or steps performed during the procedure. In some embodiments, the observation data can include data identifying the use or non-use of specific words which can indicate frustration or difficulty experienced by the surgeon during the procedure.

In addition to determining the surgeon's emotional state based on the observation data, device assessment data can be utilized to determine the efficiency, usability, and effectiveness of a particular medical device or procedure based on device assessment data that is associated with the medical device, the surgical field or clinical environment in which the medical procedure is being performed. For example, by tracking device assessment data associated with the on-screen activity, such as a scope view of the meniscal repair procedure, as well as observation data of the surgeon's eye motion, the length of time between insertion of a first insertable device and removal of a second or final insertable device can be determined. The length of time can be normalized for particular insertable device. Longer times can be indicative of decreased efficiency.

In another examples, the efficiency, usability, and effectiveness of a particular medical device can be determined based on device assessment data indicating whether or not a particular device has been opened in the surgical field, but has not been successfully deployed. Additionally, or alternatively, the efficiency, usability, and effectiveness of a particular medical device can be determined based on device assessment data indicating how many times a surgeon observes the insertable device. Observing an instrument for longer periods of time can be indicative of a less efficient and less usable device. In another examples, the efficiency, usability, and effectiveness of a particular medical device can be determined based on device assessment data indicating that other medical professionals, such as a resident or fellow, are performing the procedure or parts of the procedure. More efficient and usable devices can allow medical professionals with less experience or training to perform the procedure in similar manner as a more experienced medical professional. In another examples, the efficiency, usability, and effectiveness of a particular medical device can be determined based on device assessment data indicating the presence or extent of iatrogenic cartilage damage following the meniscal repair. Less efficient and less useful devices are more likely to be associated with iatrogenic cartilage damage or other similar side-effects which can be caused by inefficient or unsafe device usage. In another examples, the efficiency, usability, and effectiveness of a particular medical device can be determined based on device assessment data indicating frequent or multiple repositioning of the patient's body. Less efficient and less useful devices may require the surgeon to adjust or otherwise reposition the patient to gain better access or perform the procedure more safely.

Examples of patient-specific inputs that can be provided to the procedure adaptation and device assessment system 300 as device assessment data to determine the efficiency, usability, and effectiveness of a particular medical device can include which the side (e.g., right or left) of the knee is being operated on, in which compartment (e.g., the medial or lateral) the meniscal tear is present, a diagnosed condition, such as the type of meniscal tear, as well as a clinical attribute of the diagnosed condition, such as the length of the tear. Examples of surgeon-specific inputs that can be provided to the procedure adaptation and device assessment system 300 as device assessment data to determine the efficiency, usability, and effectiveness of a particular medical device can include the number of years a surgeon has been attending, the number of meniscal repairs the surgeon has performed in a prior amount of time, and the number of times the surgeon has used the device in prior procedures.

While the exemplary use case is described above in regard to a meniscal repair procedure, the observation data and device assessment data can be utilized for a variety of medical procedures without limit. The observation data and device assessment data used to determine the efficiency, usability, and effectiveness of a particular medical device can be weighted and used in the procedure adaptation and device assessment system 300 to establish an assessment of a medical device. In some embodiments, the assessment can include a score regarding the efficiency, usability, and effectiveness of a particular medical device. Scores can be tabulated and compared between multiple surgeons and/or multiple medical devices or instruments in order to demonstrate objective superiority.

Figure 5:
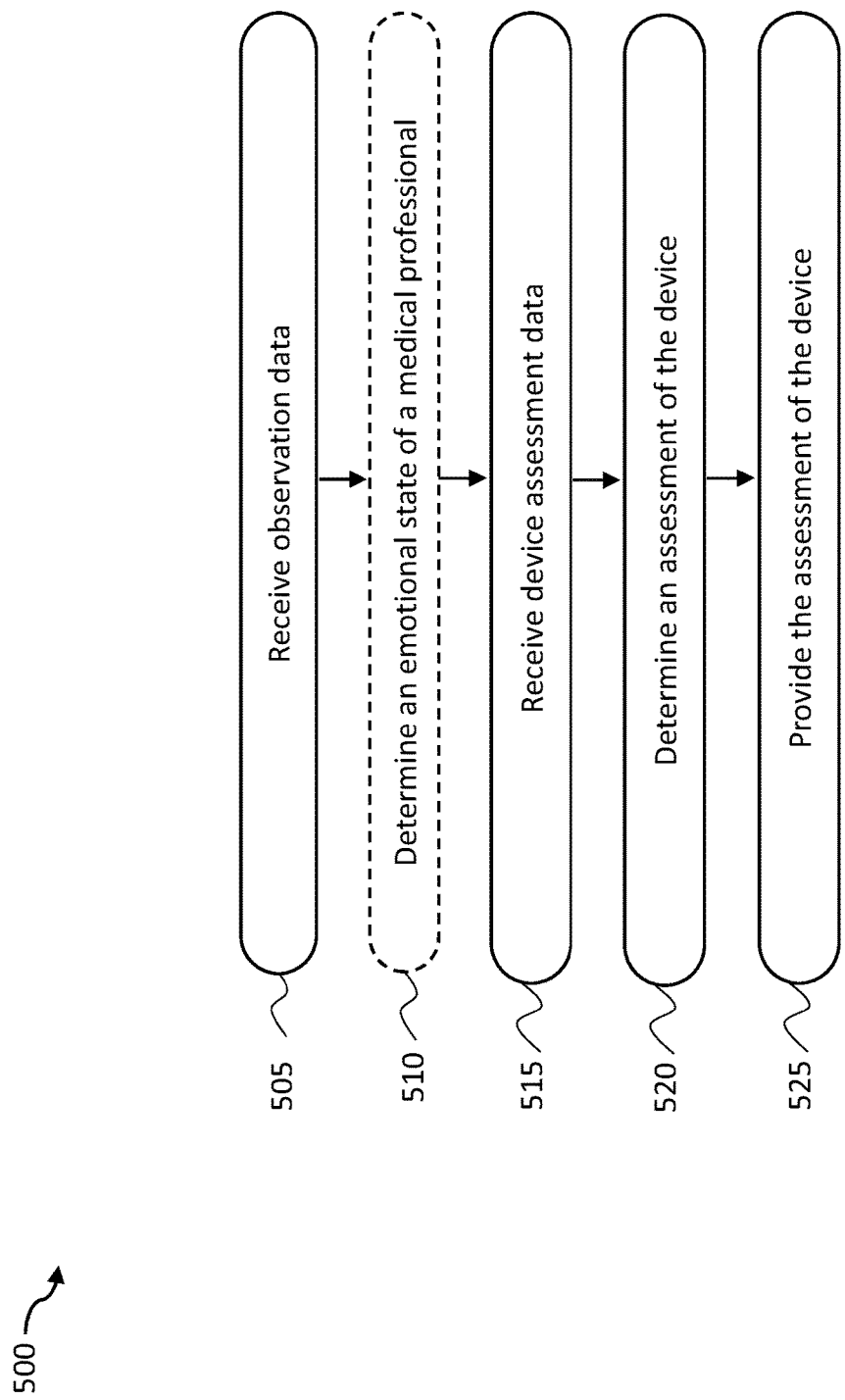
FIG. 5 is a flowchart illustrating one exemplary embodiment of a method for determining an assessment of a medical device using a determined emotional state and device assessment data using the client/server architecture of FIG. 1.

FIG. 5 is a flowchart illustrating one exemplary embodiment of a method 500 for determining an assessment of a medical device using a determined emotional state and device assessment data using the client/server architecture of FIG. 1 and the procedure adaptation and device assessment system 300 of FIG. 3. In certain aspects, embodiments of the method 500 can include greater or fewer operations than illustrated in FIG. 5 and the operations can be performed in a different order than illustrated in FIG. 5. In some embodiments, one or more of the operations of the method 500 can be performed iteratively. For example, in some embodiments, one or more of the operations can be performed one or more times prior to another one or more operations being performed. In this way, the results of individual operations can provide a feedback mechanism to generate responses over time.

For example, in operation 505, the prediction server 115 receives the operational data transmitted from one or more clients 105. The prediction server receives the operational data as described in relation to operation 405 of FIG. 4. In operation 510, as shown in dashed lines, the prediction server 115 can optionally determine an emotional state of a medical professional as described in relation to operation 410 of FIG. 4. The emotional state data 155 provided by the prediction server 115 can be transmitted to the device assessment system 170 and used to determine an assessment of a medical device.

In operation 515, the device assessment system 170 can receive device assessment data from one or more of clients 105. In some embodiments, the device assessment data can be stored in the database 110. The device assessment data can include data that is associated with the ease of use, effectiveness, utility, and usability of a particular medical device or procedure. In some embodiments, device assessment data can include observation data that is observing a medical professionals physical attributes, motions, or voice. In some embodiments, the device assessment data can include observation data observing a medical professionals use of a particular instrument, device, piece of equipment, or the like. In some embodiments, the device assessment data can include data observing the use, function, operation, deployment, or non-use of a particular instrument, device, and piece of equipment itself. The device assessment data can also include patient-specific data such as patient orientation within the surgical field or procedure environment, the region or location on the patient's body in which the procedure is occurring, as well as diagnostic data about the medical condition or clinical issue for which the procedure is intended to address. The device assessment data can also include surgeon-specific data such as the training level or experience of the medical professional performing the procedure, the number of times the medical professional has performed the procedure, or the like.

In operation 520, the device assessment system 170 processes the device assessment data (as well as other observation data), to determine an assessment of the device. In some embodiments, in operation 520, the device assessment system 170 can optionally process the emotional state that may have been determined in operation 510 in addition to the device assessment data and/or the observation data. For example, the device assessment system 170 can include an algorithm or computational model configured to receive device assessment data, and/or observation data as inputs and to provide an assessment of the medical device based on the received inputs. In some embodiments, the device assessment system 170 can optionally receive determined emotional state data 155 which can also be used to provide the assessment of the medical device. The input parameters of the algorithm can be weighted to account for the priority or importance that a particular input parameter may assigned. For example, device assessment data corresponding to a number of un-used (e.g. not deployed) devices may be weighted high, while device assessment data corresponding to the side of a patient's knee on which a procedure is to occur may be weighted low. Based on the inputs, the device assessment system 170 determines a quantitative measure of the efficiency, usability, and effectiveness of a particular medical device. The quantitative measure can be computed, for example, as a score, and can be further aggregated for multiple medical professionals and for multiple types of medical devices.

In operation 525, the device assessment system 170 provides the assessment of the device. For example, the device assessment system 170 can output the device assessment scores to one or more clients 105, which can include a display to present the device assessment score. In some embodiments, the device assessment and scores can be output to the database 110, or the like.

The improved procedure adaptation and device assessment system described herein addresses the technical problem of efficiently generating determined emotional states of medical professionals and predicting clinical procedures adaptations based on the observation data. The problem of determining and generating clinical procedure modifications or adaptations based on a medical professionals emotional state can be difficult and error-prone, requiring significant time to evaluate or survey the medical professional for their emotional state. The exemplary technical effects of the methods, systems, and computer-readable mediums described herein include, by way of non-limiting example, determining the medical professionals emotional state based on observation data and generating modified or alternate clinical procedures or sequences of actions performed within a particular clinical procedure based on observation data and/or the determined emotional state using a predictive model trained in a machine learning process. The procedure adaptation and device assessment system and the predictive model described herein provides outputs that reduce the risk of unsuccessfully performing clinical procedures by medical professionals who are not in a capable emotional state to perform a particular procedure safely and according to procedure guidelines. As a result, the rate or number of successful procedures can increase based on proactively monitoring a medical professional's emotional state and dynamically introducing changes or modifications for a particular procedure. The predictive model also provides the exemplary technical effect of reducing errors performed during a clinical procedure, ensuring clinical procedures are conducted more safely, ensuring proper equipment usage, and providing training materials and/or equipment alternatives in real-time to the medical professional during the clinical procedure. Thus the system represents an improvement of computer functionality that processes observation data, determines an emotional state of a medical professional, and provides adaptations in clinical procedures in which the medical professional is participating.

Additionally, the system 300 and the clients 105 therein can include an improved display or graphical user interface (GUI) that provides more efficient visualization and execution of the clinical procedure adaptations such as display of training materials, alternate equipment, instruments, drugs, or personnel resources, or procedure workflow modifications which can be provided to the medical professional prior to or during a procedure. The improved GUI can also provide enhanced visualizations for responding to alerts or notifications for anomalous emotional states or failed conformance with adapted clinical procedures. Existing systems used to monitor and modify procedural workflows in a clinical setting typically do not monitor an emotional state of a medical professional and do not include such robust interfaces to provide the adapted clinical procedure data provided by a trained prediction model. Existing procedure monitoring systems or applications are limited to monitoring the number of hours a medical professional has been on call or may include manual methods to ensure conformance with procedure protocols, such as completing checklists of procedural tasks by observing a medical professional during a procedure. The improved procedure adaptation and device assessment system provides a predictive, automated, user-configurable procedure monitoring and adaptation system capable of determining an emotional state of a medical professional and generating training support, alternate equipment selections, environment modifications, and/or workflow alternatives to sequences of actions associated with a particular clinical procedure based on inputs that may include minimal indications of such adaptations in the observation data used as inputs to the system.

The improved procedure adaptation and device assessment system described herein further addresses the technical problem of determining an assessment of a medical device based on device assessment data and/or emotional state data. Often, device assessments are determined based on subjective feedback which may be provided by a medical professional during or after performing a medical procedure which do not take into account the emotional state of the medical professional and thus may not represent an accurate characterization of the device. The exemplary technical effects of the methods, system and computer-readable mediums described herein include, by way of non-limiting example, determining the medical professionals emotional state based on observation data and determining an assessment of a medical device based on the determined emotional state and based on device assessment data that can be associated with observations or observation data collected during a medical procedure. The procedure adaptation and device assessment system provides device assessments as qualitative measures that can be used to inform hospital administrators, device manufacturers, procedure training personnel, and medical professionals participating in a particular medical procedure about the efficiency, usability, and effectiveness of a particular medical device. As a result, medical devices may be selected for use which are more likely to be favored by the medical professionals employing them which can result in a greater likelihood of performing medical procedures successfully and safely. Thus the system represents an improvement of computer functionality that processes observation data to determine an emotional state of a medical professional and utilizes that determined emotional state with device assessment data to provide an assessment of a medical device.

Certain exemplary embodiments have been described to provide an overall understanding of the principles of the structure, function, manufacture, and use of the systems, devices, and methods disclosed herein. One or more examples of these embodiments have been illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-named components of the embodiments generally have similar features, and thus within a particular embodiment each feature of each like-named component is not necessarily fully elaborated upon.

The subject matter described herein can be implemented in analog electronic circuitry, digital electronic circuitry, and/or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine-readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., a GPU (graphical processing unit), an FPGA (field programmable gate array) or an ASIC (application-specific integrated circuit).

Processors suitable for the execution of a computer program include, by way of example, both general and special purpose microprocessors, and any one or more processor of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The techniques described herein can be implemented using one or more modules. As used herein, the term "module" refers to computing software, firmware, hardware, and/or various combinations thereof. At a minimum, however, modules are not to be interpreted as software that is not implemented on hardware, firmware, or recorded on a non-transitory processor readable recordable storage medium (i.e., modules are not software per se). Indeed "module" is to be interpreted to always include at least some physical, non-transitory hardware such as a part of a processor or computer. Two different modules can share the same physical hardware (e.g., two different modules can use the same processor and network interface). The modules described herein can be combined, integrated, separated, and/or duplicated to support various applications. Also, a function described herein as being performed at a particular module can be performed at one or more other modules and/or by one or more other devices instead of or in addition to the function performed at the particular module. Further, the modules can be implemented across multiple devices and/or other components local or remote to one another. Additionally, the modules can be moved from one device and added to another device, and/or can be included in both devices.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected by any form or medium of digital data communication, e.g., a communication network. Examples of communication networks include a local area network ("LAN") and a wide area network ("WAN"), e.g., the Internet.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

One skilled in the art will appreciate further features and advantages of the invention based on the above-described embodiments. Accordingly, the present application is not to be limited by what has been particularly shown and described, except as indicated by the appended claims. All publications and references cited herein are expressly incorporated by reference in their entirety.

The invention claimed is:

1. A method comprising:
training a predictive model configured on a first computing system to determine adaptations of a clinical procedure performed by a medical professional in an operating room using an instrument, the predictive model trained using observation data associated with the medical professional performing the clinical procedure using the instrument, the observation data including image data acquired via a camera sensor configured within the operating room and having a field of view of the medical professional's hands and face, the observation data further including instrument data acquired via an instrument sensor configured in the instrument;
configuring a trained predictive model on a second computing system configured in an operating room configured with a camera sensor in which a first medical professional is performing a clinical procedure, the trained predictive model corresponding to the predictive model trained on the first computing system;
receiving, by the trained predictive model, observation data associated with the medical professional performing the clinical procedure in the operating room using an instrument, the observation data including instrument data acquired by an instrument sensor configured within the instrument held by the medical professional during the clinical procedure and image data acquired by the camera sensor having a field of view including the instrument and the medical professional's hands and face, the instrument sensor and the camera sensor communicatively coupled to the second computing system;
determining, by the trained predictive model, at least one adaptation of the clinical procedure based on the received observation data, the at least one adaptation including training materials identifying a preference of the medical professional observed during the clinical procedure;
providing, by the second computing system, the at least one adaptation on a display of the second computing system, the at least one adaptation provided as ghost images acquired during previous instances of the clinical procedure performed by the medical professional, the ghost images overlaid atop camera data acquired as the medical professional performs the clinical procedure.

2. The method of claim 1, wherein the observation data is further received from a sensor configured within an article of personal protective equipment worn by the medical professional during the clinical procedure.

3. The method of claim 1, wherein the observation data includes one or more of thermal imaging data, eye motion data, or survey data collected from the medical professional during the clinical procedure.

4. The method of claim 1, wherein the observation data is received from a piece of equipment used within the operating room.

5. The method of claim 1, wherein the predictive model is further trained to associate facial image data acquired by the camera sensor with at least one emotional state of the medical professional including fear, anger, sadness, joy, disgust, trust, anticipation, surprise, love, remorse, sorrow, depression, excitement, anxiety, ambivalence, boredom, interest, violence, distraction, fatigue, surprise, or apprehension.

6. The method of claim 1, further comprising transmitting the at least one adaptation to a client device communicatively coupled to the second computing system, wherein the transmitting is performed by at least one data processor of the second computing system.

7. The method of claim 1, wherein the at least one adaptation further includes one or more of generating an alert or notification, providing alternate or additional personnel resources, adjusting lighting within the operating room, and adjusting a temperature of the operating room.

8. The method of claim 1, wherein the observation data and/or the at least one adaptation are provided as inputs to a medical training assessment system, a medical resource allocation system, and/or a medical billing system.

9. A system comprising:
an instrument configured for use during a clinical procedure performed by a medical professional within an operating room, the instrument including an instrument sensor configured to acquire instrument data associated with usage of the instrument during the clinical procedure;
a camera sensor configured in the operating room to acquire image data and having a field of view including the instrument and the medical professional's hands and face,
a first computing device including a first data processor and a first memory storing computer-readable instructions, which when executed cause the first data processor to perform operations comprising
training a predictive model to determine adaptations of a clinical procedure performed by a medical professional in an operating room using an instrument, the predictive model trained using observation data associated with the medical professional performing the clinical procedure using the instrument, the observation data including image data acquired via a camera sensor configured within the operating room and having a field of view of the medical professional's hands and face, the observation data further including instrument data acquired via an instrument sensor configured in the instrument; and
a second computing device configured in the operating room and communicatively coupled to the first computing device, an instrument including an instrument sensor configured therein, and a camera sensor, the second computing device including a second data processor, a display, and a second memory storing computer-readable instructions, the second data processor configured to execute the computer-readable instructions stored in the second memory, which when executed, cause the second data processor to perform operations including
configuring a trained predictive model received from the first computing device on the second computing device, the trained predictive model corresponding to the predictive model trained on the first computing system,
receiving, by the trained predictive model, observation data associated with the medical professional performing the clinical procedure in the operating room using the instrument, the observation data including instrument data acquired by the instrument sensor as the instrument is held by the medical professional during the clinical procedure and image data acquired by the camera sensor and including images of the instrument and the medical professionals hands and face;
determining, by the trained predictive model, at least one adaptation of the clinical procedure based on the observation data, the at least one adaptation including training materials identifying a preference of the medical professional observed during the clinical procedure; and
providing, by the second computing device, the at least one adaptation on the display of the second computing system, the at least one adaptation provided as ghost images acquired during previous instances of the clinical procedure performed by the medical professional, the ghost images overlaid atop camera data as the medical professional performs the at least one action requiring verification.

10. The system of claim 9, wherein the observation data includes one or more of thermal imaging data, eye motion data, or survey data collected from the medical processional during the clinical procedure.

11. The system of claim 9, wherein the predictive model is further trained to associate facial image data acquired by the camera sensor with at least one emotional state of the medical professional including fear, anger, sadness, joy, disgust, trust, anticipation, surprise, love, remorse, sorrow, depression, excitement, anxiety, ambivalence, boredom, interest, violence, distraction, fatigue, surprise, or apprehension.

12. The system of claim 9, wherein the second data processor is further configured to perform operations including transmitting the at least one adaptation to a client device coupled to the second computing device.

13. A method comprising:
training a predictive model configured on a first computing system to determine an efficiency score corresponding to an instrument used in a clinical procedure performed by a medical professional in an operating room using the instrument, the predictive model trained to generate the efficiency score as a quantitative value indicative of the medical professional's efficiency utilizing the instrument using observation data and device assessment data associated with the medical professional performing the clinical procedure using the instrument, the observation data including camera data including image data acquired via a camera sensor configured within the operating room and having a field of view of the medical professional's hands and face, the observation data further including instrument data acquired via an instrument sensor configured in the instrument;
configuring a trained predictive model on a second computing system configured in an operating room configured with a camera sensor in which a medical professional is performing a clinical procedure, the trained predictive model corresponding to the predictive model trained on the first computing system;
receiving, by the second computing system, observation data associated with a first sequence of actions performed by the medical professional performing a clinical procedure in the operating room, the observation data including instrument data acquired by an instrument sensor configured within an instrument used in the clinical procedure and image data acquired by a camera sensor configured within the operating room and having a field of view including the instrument and the medical professional's hands and face, the instrument sensor and the camera sensor communicatively coupled to the computing system;
receiving, by the trained predictive mode, device assessment data associated with usage of the instrument by the medical professional during the first sequence of actions of the clinical procedure, the device assessment data including orientation data corresponding to a position of the instrument within relative to a position of a patient within a surgical field of the medical procedure;
determining, by the trained predictive model, an efficiency score corresponding to use of the instrument;
providing, by a display of the second computing system in the operating room, the efficiency score of the instrument as the medical professional performs the first sequence of actions of the clinical procedure.

14. The method of claim 13, wherein the model is further configured to determine the efficiency score based on facial image data acquired by the camera sensor and associated with at least one emotional state of the medical professional including fear, anger, sadness, joy, disgust, trust, anticipation, surprise, love, remorse, sorrow, depression, excitement, anxiety, ambivalence, boredom, interest, violence, distraction, fatigue, surprise, or apprehension.

15. The method of claim 13, wherein the device assessment data includes one or more of medical professional assessment data, or surgical field assessment data.

16. The method of claim 15, wherein the device assessment data further includes one or more of a location on the patient's body, a side of the patient's body on which the clinical procedure is occurring, a diagnosed condition of the patient, or a clinical attribute of a diagnosed condition of the patient.

17. The method of claim 15, wherein the medical processional assessment data includes one or more of an amount of educational experience of the medical professional performing the clinical procedure, an amount of procedural experience of the medical professional performing the clinical procedure, an amount of procedural experience of the medical professional performing the clinical procedure using the instrument.

18. The method of claim 13, wherein the observation data is further received from a galvanic skin response sensor, a perspiration sensor, a piece of equipment used during the clinical procedure, and/or a piece of personal protective equipment worn by the medical professional during the clinical procedure.

19. The method of claim 13, wherein the device assessment data includes survey data collected from the medical professional during the clinical procedure.

* * * * *